United States Patent
Kuperman

(10) Patent No.: US 10,383,703 B2
(45) Date of Patent: Aug. 20, 2019

(54) SYSTEM AND METHOD FOR MANUFACTURING CROWNS FOR TEETH

(71) Applicant: Tal Kuperman, Lake Worth, FL (US)

(72) Inventor: Tal Kuperman, Lake Worth, FL (US)

( * ) Notice: Subject to any disclaimer, the term of this patent is extended or adjusted under 35 U.S.C. 154(b) by 0 days.

(21) Appl. No.: 15/902,719

(22) Filed: Feb. 22, 2018

(65) Prior Publication Data

US 2018/0235728 A1 Aug. 23, 2018

Related U.S. Application Data

(60) Provisional application No. 62/462,668, filed on Feb. 23, 2017, provisional application No. 62/477,214, filed on Mar. 27, 2017.

(51) Int. Cl.

| | |
|---|---|
| *A61C 5/77* | (2017.01) |
| *A61C 13/20* | (2006.01) |
| *A61C 13/34* | (2006.01) |
| *A61C 8/00* | (2006.01) |
| *A61C 13/00* | (2006.01) |

(52) U.S. Cl.
CPC .............. *A61C 5/77* (2017.02); *A61C 8/0001* (2013.01); *A61C 13/20* (2013.01); *A61C 13/0006* (2013.01); *A61C 13/34* (2013.01)

(58) Field of Classification Search
CPC ......... A61C 5/77; A61C 8/0001; A61C 13/20; A61C 13/0006; A61C 13/34
See application file for complete search history.

(56) References Cited

U.S. PATENT DOCUMENTS

| | | | | |
|---|---|---|---|---|
| 3,423,828 | A | * | 1/1969 | Halpern ............... A61C 13/087 433/202.1 |
| 4,214,356 | A | | 7/1980 | Takenaka et al. |
| 4,321,042 | A | * | 3/1982 | Scheicher ............ A61C 8/0012 433/201.1 |
| 4,767,331 | A | | 8/1988 | Hoe |
| 6,190,171 | B1 | | 2/2001 | Hajjar et al. |
| 2005/0023710 | A1 | * | 2/2005 | Brodkin ............. A61C 13/0003 264/16 |
| 2005/0227203 | A1 | | 10/2005 | Kuperman |
| 2007/0037127 | A1 | | 2/2007 | Ibsen et al. |
| 2009/0298016 | A1 | * | 12/2009 | Chu .................... A61C 13/0006 433/203.1 |
| 2014/0242540 | A1 | * | 8/2014 | Jones ...................... A61C 9/00 433/71 |

* cited by examiner

*Primary Examiner* — Wade Miles
*Assistant Examiner* — Drew S Folgmann
(74) *Attorney, Agent, or Firm* — Robert M. Downey, P.A.

(57) ABSTRACT

A system and method for fabricating dental crowns and bridgework includes the steps of: selecting one or more prototype teeth; forming a mold around the prototype teeth using a soft flexible material; placing the mold within a model of a patient's teeth; pressing the uppers and lowers of the model together to establish the bite; removing the prototype teeth from the mold; adding wet porcelain to the inside walls of the mold and vibrating the mold to create the incisal; adding wet porcelain to create the body; pressing framework into the uncured body; vibrating the mold and removing moisture; allowing the porcelain to dry and removing the molded porcelain crown or bridgework from the mold; trimming off excess porcelain and adding porcelain to the margin area as needed; baking the crown or bridgework in an oven and removing when half cured; and carving and shaping the half cured porcelain.

6 Claims, No Drawings

SYSTEM AND METHOD FOR MANUFACTURING CROWNS FOR TEETH

This non-provisional patent application is based on provisional patent application Ser. No. 62/462,668 filed Feb. 23, 2017 and provisional patent application Ser. No. 62/477,214 filed Mar. 27, 2017.

BACKGROUND OF THE INVENTION

Field of the Invention

The present invention is directed to a system and method for fabricating dental crowns and bridgework, and more particularly to a system and method that greatly reduces the time and simplifies the task of fabricating highly aesthetic dental crowns and bridgework that have excellent shape and anatomy and vital florescence.

Discussion of the Related Art

The fabrication of crowns and bridges has always been a time consuming and expensive process, requiring a considerable amount of skilled (artisan) labor to custom fit crowns and bridges for each case. Traditionally, a technician is required to prepare a pasty mixture of a ceramic powder and a liquid which gradually dries into a packed powder. While it is drying, the technician must mold and carve the pasty mixture into a shape resembling the natural tooth it is replacing, or in the case of an all ceramic crown, the technician must also match the contours of the tooth stump to which it is to be affixed. Not only is the shaping operation time consuming and difficult, but there is also the problem of the proper blending of colors in order to match the color of the teeth to each other or to those natural teeth adjacent to the one being fabricated. In many instances, the resultant fabricated crown or bridge does not have a vital appearance and is easily discernible from the remaining teeth.

SUMMARY OF THE INVENTION

A system for fabricating dental crowns and bridgework uses a silicon composition or like soft and pliable material that is easily formed in less than ten minutes. The soft material is molded over real teeth or artificial teeth (either being referred to hereinafter as "prototype teeth" or "prototype tooth") to create a crown mold and a bite mold. This provides the desired perfect anatomical shape. The soft crown or bridgework mold is then placed within a prefabricated model of the patients teeth. Next, the upper and lower teeth of the model are pressed together so that the soft mold engages the opposing teeth of the model. This establishes the bite of the opposing teeth and perfect shape crown or bridgework. The prototype tooth (for a crown) or prototype teeth (for a bridge) is then removed from the soft mold and wet porcelain is placed in the mold. Next, the mold is vibrated to create the incisal in a thin layer to include the occlusal, buccal, lingual, and facial walls. The body (i.e., more wet porcelain) is then added to the mold and vibrated using a variable speed vibration machine. Next, framework is pressed into the wet porcelain or other material forming the body until it reaches the established point or margin area. The mold is vibrated and moisture is removed from the wet porcelain. This can be done using a tissue. Once the porcelain is dry, the molded porcelain crown or bridgework is removed by opening the flexible mold and pushing the new teeth (i.e., crown or bridgework) out of the soft mold. Excess porcelain is cut away along the lower margin area and porcelain can be added to the margin area as needed. The molded porcelain crown or bridgework is then baked in a porcelain oven for between 40 percent to 70 percent of the cure time. The porcelain crown/bridgework is then removed when partially cured so that the porcelain material is still soft and easy to shape and carve to adjust the bite if needed for completion. In another embodiment of the invention, a block formation or overbuilt (exaggerated build-up) crown or bridgework (i.e., single unit or multiple unit) is molded using the soft mold, and is removed from the oven at 50%-80% of the cure time. Next, a CAD cam system is used to allow precision cutting and formation by a milling machine so that no hand work is needed. In either embodiment, the crown/bridgework can be glazed back into the oven for completion.

OBJECTS AND ADVANTAGES OF THE INVENTION

Considering the forgoing, it is a primary object of the present invention to provide a system for producing dental crowns and bridges that eliminates between fifty percent and eighty percent of the labor normally involved in the currently used processes of producing dental crowns and bridges.

It is a further object of the present invention to provide a system for producing dental crowns and bridges that produces perfectly shaped and anatomically correct crowns and bridges to provide an extremely natural appearance.

It is a further object of the present invention to provide a system for producing dental crowns and bridges of the desired aesthetically vital color that match the shade guide.

It is a further object of the present invention to provide a system for producing dental crowns and bridges with high quality control.

It is a further object of the present invention to provide a system for producing dental crowns and bridges that are vital fluorescent.

It is a further object of the present invention to provide a system for producing dental crowns and bridges having high end aesthetics.

It is a further object of the present invention to provide a system for producing dental crowns and bridges that allows an average dental ceramist to create dental crowns and bridges that are on the level of a highly skilled artisan in the field of dental prosthetics in less than half the time normally required by a skilled artisan to create dental crowns and bridges using existing techniques, materials, machinery and systems.

It is a further object of the present invention to provide a system for producing dental crowns and bridges which eliminates the need for grinding and buildup, as well as unnecessary waste of materials (e.g., porcelain).

It is a further object of the present invention to provide a system for producing dental crowns and bridges which eliminates the need for multiple bakes in a porcelain oven.

It is a further object of the present invention to provide a system for producing dental crowns and bridges which eliminates the need to carve the anatomy into the crown or bridgework with a high speed air turbine or brush.

It is a further object of the present invention to provide a system for producing dental crowns and bridges which creates perfect anatomically correct buccal, lingual and facial walls that are extremely vital and natural in appearance.

It is a further object of the present invention to provide a system for producing dental crowns and bridges that saves fifty percent to eighty percent of time compared to existing techniques and systems in the related art.

It is a further object of the present invention to provide a system for producing dental crowns and bridges which can be used to create a single unit (i.e., crown for one tooth) or multiple units, as well as a full mouth rehabilitation including upper and lower bridgework.

It is a further object of the present invention to provide a system for producing dental crowns and bridges wherein the incisal can be pressed by the oven a first time and a body of the crown can be pressed during a second time or process for individual blending of different incisals and porcelain effect colors.

It is a further object of the present invention to provide a system for producing dental crowns and bridges that can be used with any dental porcelain product on the market.

It is a further object of the present invention to provide a system for producing dental crowns and bridges that can be used with metal crowns and bridges or ceramic crowns and bridges.

It is a further object of the present invention to provide a system for producing dental crowns and bridges that can be used on zirconia coping while being very vital and aesthetically pleasing.

It is a further object of the present invention to provide a system for producing dental crowns and bridges wherein a block formation or overbuilt (i.e., exaggerated size) tooth formation is molded in a soft mold and then 60%-80% cured at which time the final crown or bridgework is cut by a milling machine with the use of a CAD CAM system.

It is a further object of the present invention to provide a system for producing dental crowns and bridges that separates interproximal area on bridgework and rounds off teeth perfectly which saves a significant amount of bench time and eliminates the need for multiple bakes in a porcelain oven.

These and other objects and advantages of the present invention are more readily apparent with reference to the following detailed description.

DETAILED DESCRIPTION OF THE PREFERRED EMBODIMENT

The present invention is directed to a system and method for fabricating dental crowns and bridgework. To begin, real teeth or artificial teeth (i.e., "prototype teeth") are selected for a particular patient that will be fitted with the fabricated crown or bridgework. The prototype tooth or teeth are selected to match the anatomy of the patient and should be slightly larger to allow for shrinking of the porcelain material during fabrication of the crown or bridgework. Next, a silicon composition or like soft and pliable material is molded over the prototype teeth to establish a crown and bite mold that provides the desired perfect anatomical shape. The soft mold is then placed within a prefabricated model of the patient's teeth that has upper and lower teeth replicating the patient's upper and lower teeth. Next, the upper and lower teeth of the model are pressed together to establish the bite of the opposing teeth and perfect shape crown or bridgework. The prototype tooth (or teeth) is then removed from the soft mold and a layer of wet porcelain is applied to the inner walls of the mold where the prototype tooth was removed (i.e., the mold cavity). Next, the mold is vibrated to create the incisal in a thin layer to include the occlusal, buccal, lingual, and facial walls. Next, more porcelain material for the body is added to the mold and vibrated using a variable speed vibration machine. The framework is then pressed into the wet porcelain or other material forming the body until it reaches the established point or margin area. The framework is prefabricated to be congruent with the shape of the patient's tooth stump to which the crown or bridge is to be affixed. The mold is vibrated and moisture is removed from the wet porcelain using a tissue or other method. Once the porcelain is dry, the molded porcelain crown or bridgework is removed from the mold by opening the flexible mold and pushing the new teeth (i.e., crown or bridgework) out of the soft mold and into a tissue. Excess porcelain is cut away along the lower margin area and porcelain can be added to the margin area as needed. The molded porcelain crown is then baked in a porcelain oven for between forty percent and seventy percent of the cure time. The porcelain crown/bridgework is then removed when partially cured so that the porcelain material is still soft and easy to shape and carve to adjust the bite if needed for completion. In another embodiment of the invention, a block formation or overbuilt (exaggerated build-up) crown or bridgework (i.e., single unit or multiple unit) is molded using the soft mold, and is removed from the oven at 50%-80% of the cure time. Next, a CAD CAM system is used to allow precision cutting and formation by a milling machine so that no hand work is needed. In either embodiment, the crown/bridgework can be glazed back into the oven for completion.

While the present invention has been shown and described in accordance with a preferred and practical embodiment, it is recognized that departures from the instant disclosure are fully contemplated within the spirit and scope of the present invention which is not to be limited, except as defined in the following claims as interpreted under the Doctrine of Equivalents.

What is claimed is:

1. A method for fabricating dental crowns or bridgework comprising the steps of:
   selecting at least one model tooth;
   forming a flexible mold around the selected model tooth using a soft, pliable and flexible molding material;
   removing the at least one model tooth from the flexible mold to provide a mold cavity for forming the dental crown or bridgework;
   applying a layer of wet porcelain material to inside walls of the mold cavity;
   vibrating the flexible mold and the layer of the porcelain material to form an incisal of the crown or bridgework;
   adding wet porcelain material to at least partially fill the formed incisal and thereby providing a body of the crown or bridgework;
   pressing prefabricated framework into the wet porcelain material that provides the body;
   vibrating the flexible mold and removing moisture from the wet porcelain material;
   removing the molded porcelain crown or bridgework with the prefabricated framework from the flexible mold prior to curing by opening the flexible mold and pushing the molded porcelain crown or bridgework out of the flexible mold;
   placing the removed molded crown or bridgework in a porcelain oven without the flexible mold and baking the molded crown or bridgework to at least partially cure the porcelain material; and
   removing the molded crown or bridgework from the porcelain oven.

2. The method as recited in claim 1 wherein the step of selecting at least one model tooth further comprises the steps of:
- placing one or more model teeth in a prefabricated model of the patient's teeth in the location where the crown or bridgework is to be fitted;
- comparing the one or more model teeth to adjacent and opposing teeth in the prefabricated model; and
- selecting the at least one model tooth that conforms with the size, shape and anatomy of the patient's adjacent and opposing teeth as replicated on the prefabricated model.

3. The method as recited in claim 1 further comprising the step of:
- trimming off excess porcelain along a lower margin area of the crown or bridgework after the step of removing the molded porcelain crown or bridgework from the mold.

4. The method as recited in claim 1 further comprising the step of:
- adding porcelain along a lower margin area of the crown or bridgework after the step of removing the molded porcelain crown or bridgework from the mold.

5. The method as recited in claim 1 further comprising the steps of:
- carving and shaping the molded crown or bridgework to final form after removing the molded crown or bridgework from the porcelain oven; and
- placing the molded crown or bridgework in the porcelain oven for a second bake after the step of carving and shaping the molded crown or bridgework.

6. A method for fabricating dental crowns or bridgework comprising the steps of:
- forming a flexible mold using a soft, pliable and flexible molding material to create an exaggerated size mold cavity;
- applying a layer of wet porcelain material to inside walls of the mold cavity for forming an exaggerated size molded crown or bridgework;
- vibrating the flexible mold to create and the layer of the porcelain material to form an incisal of the crown or bridgework;
- adding wet porcelain material to at least partially fill the formed incisal and thereby providing a body of the crown or bridgework;
- pressing prefabricated framework into the wet porcelain material that provides the body;
- vibrating the flexible mold and removing moisture from the wet porcelain material;
- removing the exaggerated size molded porcelain crown or bridgework with the prefabricated framework from the flexible mold prior to curing by opening the flexible mold and pushing the molded porcelain crown or bridgework out of the flexible mold;
- placing the removed exaggerated size molded crown or bridgework in a porcelain oven without the flexible mold and baking the molded crown or bridgework until the porcelain material is between 50% and 80% cured;
- removing the exaggerated size molded crown or bridgework from the oven with the porcelain material partially cured; and
- using a CAD CAM system for precision cutting and formation of the molded porcelain crown or bridgework using a milling machine.

* * * * *